United States Patent [19]
Carlson

[11] Patent Number: 5,637,168
[45] Date of Patent: Jun. 10, 1997

[54] APPARATUS AND METHOD FOR MAKING FLEXIBLE TUBING WITH HELICALLY WOUND HEATING CONDUCTOR

[75] Inventor: Lennart L. Carlson, Irvine, Calif.

[73] Assignee: Steward Plastics, Inc., Laguna Hills, Calif.

[21] Appl. No.: 507,732

[22] Filed: Jul. 26, 1995

Related U.S. Application Data

[62] Division of Ser. No. 250,173, May 27, 1994, Pat. No. 5,454,061.

[51] Int. Cl.$^6$ .............................. B29C 47/02; H04B 3/40
[52] U.S. Cl. ...................... 156/143; 156/195; 156/244.15
[58] Field of Search ...................... 156/143, 195, 156/244.13, 244.15, 244.12; 392/478, 479, 480, 488, 489, 472; 219/535; 138/33

[56] References Cited

U.S. PATENT DOCUMENTS

| | | |
|---|---|---|
| Re. 29,332 | 8/1977 | Bilbro et al. . |
| 837,512 | 12/1906 | Seeley . |
| 848,238 | 3/1907 | Greenfield . |
| 1,179,578 | 4/1916 | Sundh . |
| 1,270,579 | 6/1918 | Witzenmann . |
| 2,398,876 | 4/1946 | Bailey ............................... 156/194 |
| 2,578,280 | 12/1951 | Barnard . |
| 2,602,608 | 7/1952 | Darling . |
| 2,674,297 | 4/1954 | Greenwald . |
| 2,707,491 | 5/1955 | Harris et al. . |
| 2,731,070 | 1/1956 | Meissner . |
| 2,740,427 | 8/1956 | Swan, Jr. . |
| 2,822,857 | 2/1958 | Rothermel et al. . |
| 2,846,560 | 8/1958 | Jacoby et al. . |
| 3,070,132 | 12/1962 | Sherida . |
| 3,112,771 | 12/1963 | Bringolf . |
| 3,166,688 | 1/1965 | Rowand et al. . |
| 3,173,822 | 3/1965 | Rigaut . |
| 3,252,483 | 5/1966 | Swan . |
| 3,273,600 | 9/1966 | Swan . |
| 3,275,803 | 9/1966 | True . |
| 3,290,426 | 12/1966 | Barrentine . |
| 3,301,734 | 1/1967 | Britton et al. . |
| 3,378,673 | 4/1968 | Hopper . |
| 3,494,812 | 2/1970 | Cvacho . |
| 3,645,834 | 2/1972 | McCaffrey . |
| 3,658,625 | 4/1972 | Ishikawa et al. . |
| 3,674,056 | 7/1972 | D'Aprile ............................... 138/134 |

(List continued on next page.)

FOREIGN PATENT DOCUMENTS

| | | |
|---|---|---|
| 4244493 | 7/1993 | Germany . |
| 0373174 | 12/1963 | Switzerland . |
| 373174 | 12/1963 | Switzerland ............................ 138/121 |
| 223327 | 10/1923 | United Kingdom . |
| 448933 | 12/1934 | United Kingdom . |
| 683259 | 11/1952 | United Kingdom . |
| 0799547 | 8/1958 | United Kingdom . |
| 799547 | 8/1958 | United Kingdom ............................ 392/488 |
| 897292 | 5/1962 | United Kingdom . |
| 1448473 | 9/1976 | United Kingdom . |

OTHER PUBLICATIONS

"The Clear Solution for a Complex Problem,"Tigerflex® 2001 Series, Specification, Undated, Kuriyama of America, Inc., Elk Grove Village, IL.

*Primary Examiner*—Daniel Stemmer
*Attorney, Agent, or Firm*—Oppenheimer Poms Smith

[57] ABSTRACT

A helically wound and helically ribbed plastic tubing incorporating an electrically conductive wire and an apparatus and method for making the tubing are disclosed. A plastic ribbon is wound about an axis into a tube with one edge of each lap overlapping and heat-bonded to an edge of the preceding lap as the tubing is rotated; a conductive wire is embedded in the ribbon; and a bead is applied and heat-sealed onto the tubing, encapsulating the conductive wire during rotation of the tubing, providing a unitary structure including a conductive wire integral to a flexible tubing having a corrugated crevice-free outside and a smooth inside. Coolant is applied to the tubing for cooling the unitary ribbon, wire and bead tubing and to assist in advancing the tubing along the axis.

9 Claims, 4 Drawing Sheets

U.S. PATENT DOCUMENTS

| | | | |
|---|---|---|---|
| 3,706,624 | 12/1972 | Rinker . | |
| 3,739,815 | 6/1973 | Rejeski | 138/122 |
| 3,834,423 | 9/1974 | Elson . | |
| 3,908,704 | 9/1975 | Clement et al. . | |
| 3,910,713 | 10/1975 | Maroschak . | |
| 3,910,808 | 10/1975 | Steward | 156/429 |
| 3,914,146 | 10/1975 | Koch . | |
| 3,914,147 | 10/1975 | Wienand et al. . | |
| 3,917,500 | 11/1975 | Petzetakis et al. . | |
| 3,919,026 | 11/1975 | Mizutani et al. . | |
| 3,963,856 | 6/1976 | Carlson et al. | 174/47 |
| 3,996,323 | 12/1976 | Hegler et al. . | |
| 4,038,519 | 7/1977 | Foucras . | |
| 4,118,453 | 10/1978 | Herrington . | |
| 4,120,628 | 10/1978 | Simos . | |
| 4,129,152 | 12/1978 | Davis . | |
| 4,134,958 | 1/1979 | Dunichev et al. . | |
| 4,165,214 | 8/1979 | Lupke et al. . | |
| 4,166,000 | 8/1979 | Lawson . | |
| 4,203,476 | 5/1980 | Vitellaro | 138/122 |
| 4,294,636 | 10/1981 | Vitellaro | 156/143 |
| 4,553,023 | 11/1985 | Jameson et al. . | |
| 4,686,354 | 8/1987 | Makin . | | ced
APPARATUS AND METHOD FOR MAKING FLEXIBLE TUBING WITH HELICALLY WOUND HEATING CONDUCTOR This is a divisional of application Ser. No. 08/250,173 filed on May 27, 1994, now U.S. Pat. No. 5,454,061.

BACKGROUND OF THE INVENTION

1. Field of the Invention

The present invention relates in general to plastic tubing and, more particularly, to apparatus and methods for making flexible and externally helically ribbed or beaded tubing integrally incorporating at least one electrically conductive wire.

2. Description of Related Art

Tubing having a relatively thin wall and an integral helical supporting bead is known in the art. Such support-bead tubing construction provides substantial crush resistance while leaving the tube wall flexible enough to permit short-radius bends without collapsing or kinking the tube. The versatility of this kind of tubing is evidenced by its wide applicability in construction, ventilation, manufacturing processes, auto washes, hospitals and other fields.

The walls of a support-bead tubing can be quite thin to minimize overall weight. This light weight for the tubing is an important feature, for example, in an inhalator tube to provide a patient with more comfort during oxygen delivery. Two other features of known thin wall support-bead or bead-reinforced tubing are transparency and smoothness of bore. Transparent plastic material permits inspection of the fluid coursing through the tube, to detect, for example, the presence of moisture in an anesthetic or patient oxygen delivery application. A smooth inner surface of such a tube is desirable to keep the tube free from deposits of contaminants and to discourage non-laminar flow.

U.S. Pat. No. 3,910,808 to Steward, assigned to the same assignee as this application, discloses apparatus for forming such thin-walled, flexible, crush resistant support-bead tubing. Steward discloses means for extruding a plastic strip having a longitudinal rib, and winding means for helically winding the strip about an axis to produce a corrugated flexible tubing having a smooth bore.

Many applications, however, require or are enhanced by the presence of controlled heating of such tubing. Neonatal patients, as well as patients in shock or who are sustained on breathing equipment, are among those who benefit from gas flowing through heat-conditioned tubing.

Prior attempts to achieve heating of a tube include providing: a resistance element extending linearly along the tube's axis (U.K. Patent No. 1,448,473 to Grant); fabric tape secured to a wire and applied to the tube (U.K. Patent No. 897,292 to Reik); or resistive wire in a tubing with no crush-resistant or thin-walled features (U.S. Pat. No. 4,038,519 to Foucras; U.S. Pat. No. 4,553,023 to Jameson et al.; and U.S. Pat. No. RE. 29,332 to Bilbro et al.). These tubings and those to be described in more detail in this section have one or more characteristics inconsistent with use in a medical environment. For example, tubing which relies on an adhesive binding for the support bead may deteriorate as a result of repeated sterilization. Materials may be biomedically incompatible, and exteriors are invariably characterized by crevices adjacent to the support bead which can harbor particulate matter and microbes. In addition, the more separate and distinct steps that are required in producing such tubing, the greater the cost, complexity and potential for failure of the product in use.

Another heatable tubing is described by DE 42 44 493A1 to Eilentropp. The '493A1 patent is believed to describe a respiratory tube with a spirally ribbed outer surface upon which electric heating conductors are placed adjacent to the spiral ribs. The heating conductors may be glued on to the outer surface of the tube. The ribs may be formed as a separate smaller tube profile which is then glued to the outer surface of the respiratory tube in a spiral arrangement. With a respiratory tube according to the '493A1 publication, the resistance wires must be separately secured to the outer surface of the tube, requiring a separate manufacturing step. Also, the separate glue may not provide as secure an attachment of the heating conductors to the respiratory tube as would be desired. There is a distinct possibility of imperfect match between the tube and the glue, and the glue also presents a possibility of solvents being released in the medical environment. As previously mentioned, the glue may not endure sterilization as well as the tube itself.

Finally, U.S. Pat. No. 3,686,354, issued to Makin, is believed to provide a thin-walled, flexible, but helically-ribbed collapse-resistant hose for inhalation apparatus. An inner thin-walled flexible tubular member defines a helical groove to which is helically secured an outer heater cable. The electrical heating cable is round in cross-section and is bonded to the outer surface of the tubular member by adhesive or vulcanization. With the inhalation hose according to the '354 patent, the helical heater cable does not become an integral part of the inner tubular member, but instead lays in a helical groove of the inner tubular member, defining a helical crevice on each side of the heater cable. This crevice or pair of crevices may provide an area in which soil and bacteria can escape cleaning and sterilizing efforts. Also, the heat originating at the conductors of the heater cable must be conducted through not only the insulation on this cable but also through to the wall of the inner tube. In fact, these heating conductors would appear to be more directly coupled to the ambient air than to tidal air in the tube.

No prior product, method of manufacture, or apparatus is known which provides a transparent, sterilizable, thin-walled, smooth bore tube having a resistive wire helically imbedded in the outer surface of the tube and fully protected by a contemporaneously wound supporting and encapsulating bead, the bead, wire and tube forming a unitary structure with a smooth, crevice-free outer surface.

SUMMARY OF THE INVENTION

In view of the deficiencies of the related art as discussed above, it is a primary object of the present invention to provide a flexible, lightweight, crush-resistant tubing having an electrically conductive wire and wire-supporting bead helically wound about and integral with the surface of the tubing.

It is another object of this invention to provide apparatus and method for inexpensively making a heatable tubing including resistance wire, supporting bead, and tube wall as a unitary body free of adhesive and binders and having a smoothly corrugated outer surface free of crevices.

These and other objects are achieved by the present invention which provides apparatus for combining a thin film or ribbon, a supporting bead, and a conductive wire to make a flexible tubing, and provides a method for producing the tubing in a single winding operation. The present invention employs a winding mechanism which accepts in sequence an extruded plastic flat ribbon, an electrically conductive wire and an extruded supporting bead. The ribbon is helically wrapped so that its edges overlap and simultaneously heat-bond to themselves to form a lap joint. The wire is overlaid along the overlapped edges of the ribbon and the bead is laid atop the wire and heat-bonded to the ribbon at the lap joint, forming a unitary body as described below.

While other heat-bondable plastics may be successfully used for the flat ribbon, for a variety of medical applications a polyester elastomer such as HYTREL™ 5556 is preferable for its properties including chemical purity, reusability, transparency and resistance to damage from sterilization. Thermoplastic rubbers such as SANTOPRENE® or thermoplastic elastomers such as SARLINK® are suitable materials for ribbon formation, although their transparency is inferior to that of HYTREL™. The bead material is chosen for its ability to heat-bond with the flat ribbon, and may be of the same composition as the ribbon or of a suitable compatible different composition including the materials just mentioned. For heating purposes, the wire conductor is preferably resistive metal such as nickel chromium.

Walls of the tubing are formed by overlapping, heat-bonding and cooling successive laps or convolutions of the flat ribbon as the ribbon is extruded onto canted and rotationally driven winding rolls. The present invention provides a unique wire-feeding mechanism to align the conductive wire precisely along an edge of a ribbon convolution which is sufficiently cooled to prevent the wire from cutting completely through the thin ribbon, yet still warm enough to partially embed the wire in the ribbon.

The configuration of the support bead is defined by splayed surfaces on either side of and cooperatively defining a wire-receiving recess. The surfaces are spread apart in order to form a smooth, crevice-free juncture as the bead heat-bonds to the film while the recess receives the wire, the bead thereby surrounding the wire and integrating the ribbon, wire and bead into a unitary structure.

In operation, the ribbon is extruded and helically wound onto the winding rolls from an elevated position with respect to the rolls so that any sag caused by low viscosity of the extrudate is reduced or eliminated. After several laps of the ribbon are wound on the rolls, resistance wire is paid out through the wire-feeding means to a draw point on a lap joint of the rotating workpiece where the workpiece surface is still warm enough to partially embed the wire.

Thereafter, the supporting bead is extruded over the wire on a lap joint selected so that the bead fully encapsulates the wire that is still partially embedded in the outer wall of the rotating tubing.

The unitary construction just described has a significant advantage in addition to the foregoing resistance to the accumulation of soil and bacteria and inherent supportive strength. Since a primary purpose of the tubing is to heat the tidal fluid within the bore, substantial benefit is derived by insulating the heating wire from ambient conditions, as accomplished by the encapsulating bead. Moreover, the internal fluid is separated from the heating wire by only the thin wall of the tubing, resulting in enhanced transfer of heat energy to the tidal fluid.

Further applications of the present invention will be apparent to those skilled in the art from a consideration of a fully detailed exemplary embodiment thereof. To aid in the explanation of the exemplary embodiment, reference will be made to the figures of the appended sheets of drawings, which figures will first be described briefly.

BRIEF DESCRIPTION OF THE DRAWINGS

The advantages and features of the present invention will be better understood by the following description when considered in conjunction with the accompanying drawings in which.

DETAILED DESCRIPTION OF AN EXEMPLARY EMBODIMENT

Figure 1:
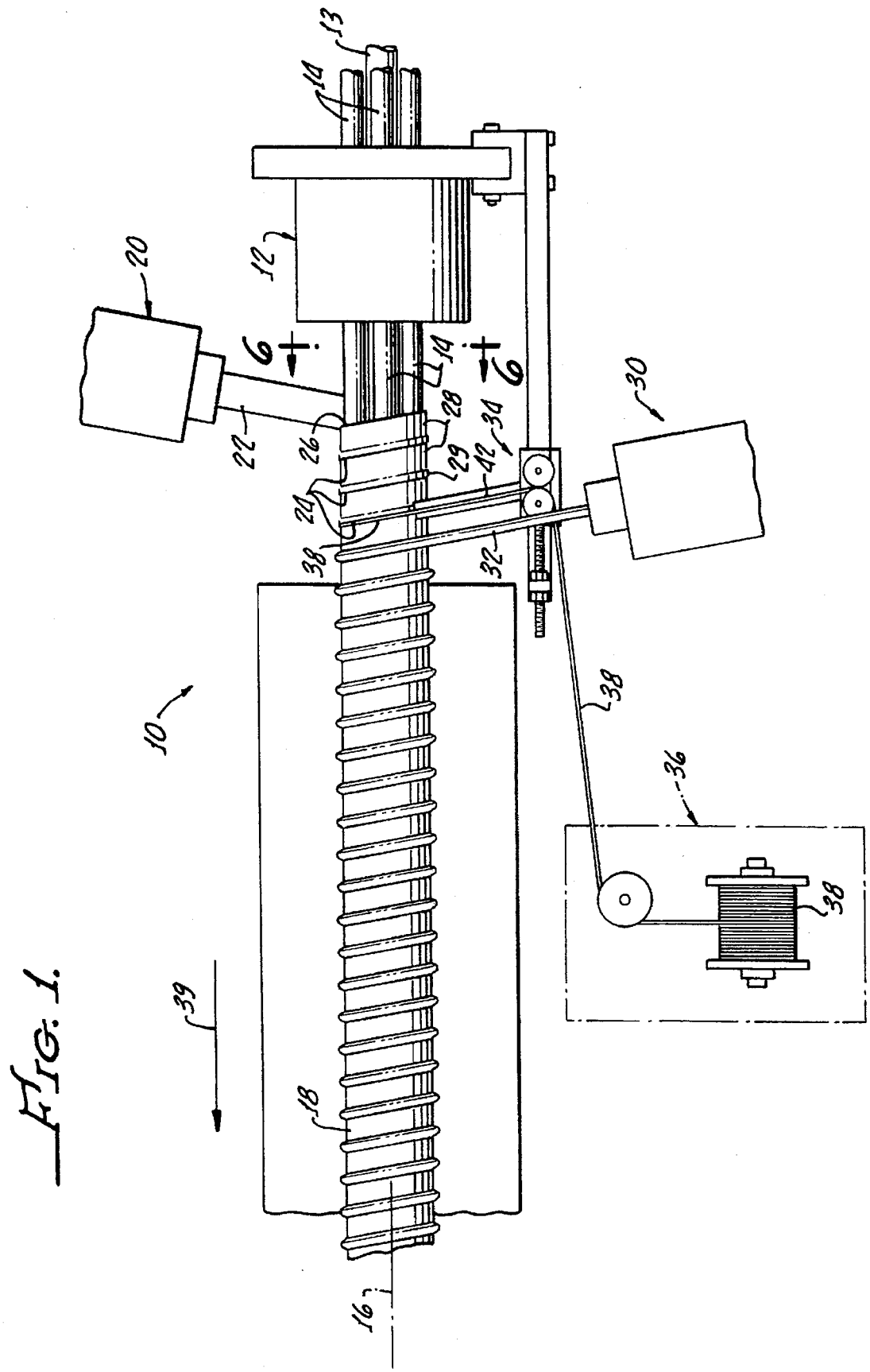
FIG. 1 is a schematic plan view illustrating the features of an exemplary embodiment of this invention and wherein parts of the apparatus are relocated for clarity of illustration.
Figure 6:
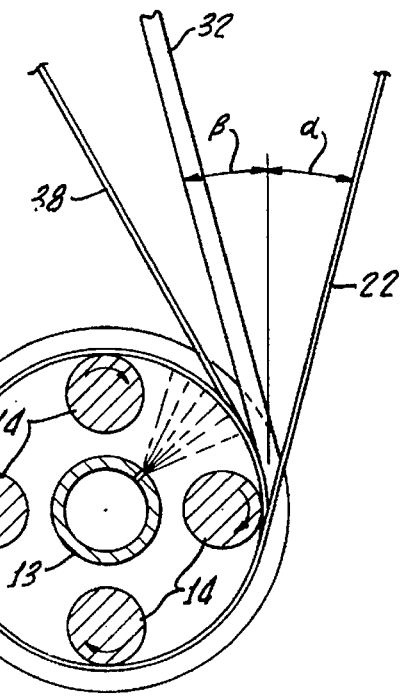
FIG. 6 is a section view taken along lines 6—6 of FIG. 1 with typical draw angles of extrudates and wire shown for clarity.
Figure 5:
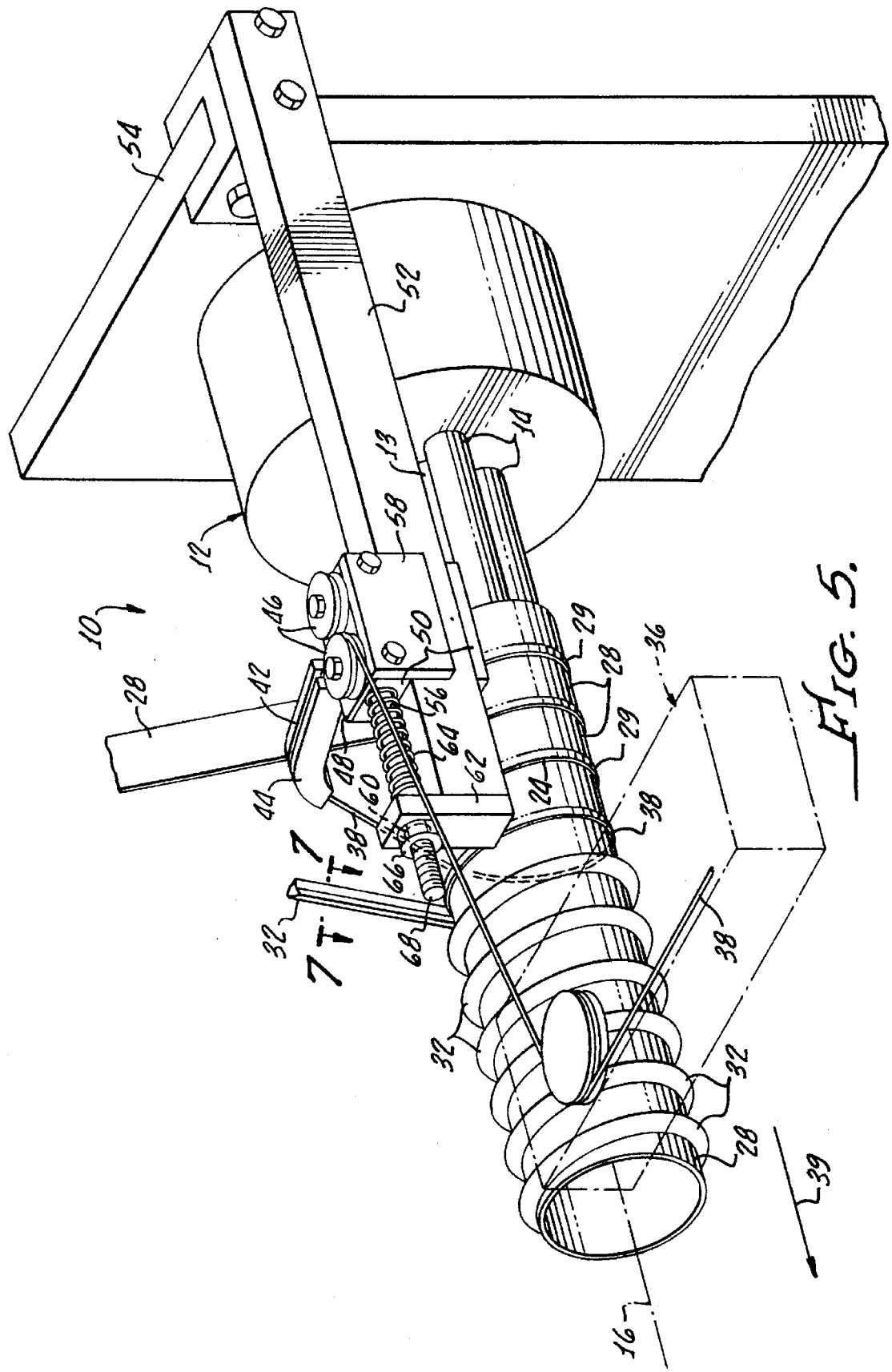
FIG. 5 is an isometric view illustrating the machine, steps in the process, and resulting product of the invention.

An embodiment of the invention including steps in the process of making the tubing product is illustrated generally in FIGS. 1 and 5. FIG. 1 illustrates apparatus 10 including winding means 12 having four cantilevered and rotationally driven winding rolls 14, canted and spaced about a longitudinal axis 16 for winding and rotationally advancing a helically wound and ribbed heatable flexible tubing 18. The rolls 14 rotate in unison in a clockwise direction as illustrated in FIG. 6.

Apparatus 10 includes also first extrusion means 20 for extruding a heat bondable flat ribbon 22 having a leading edge 24 and trailing edge 26 and second extrusion means 30 for extruding a heat bondable bead 32. Although extrusion means 20 and 30 are shown as physically separate components for ease of explanation in FIG. 1, it should be understood that both ribbon 22 and bead 32 may be extruded from co-located dies corresponding to very small draw angles as described later with reference to FIG. 6.

Figure 2:
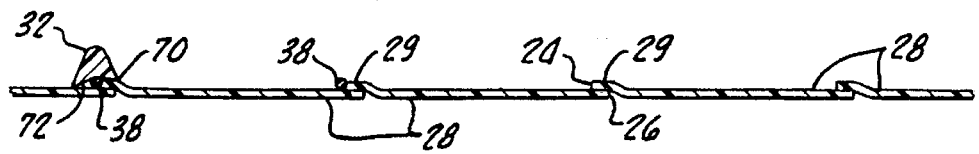
FIG. 2 is a schematic illustration of a workpiece cross-section showing the sequential placement of the lap joint bonded ribbon, wire, and external support-bead feature of the invention.

Ribbon 22 is wrapped about the rolls 14 and is advanced helically toward the left, viewing FIGS. 1 and 5, so that it encircles the rolls 14 and wraps upon itself with a certain overlap, as seen in FIG. 2, to form successive convolutions 28. The adjacent convolutions or laps of the film 22 are heat-bonded to adjacent convolutions at a lap joint 29 cooperatively defined by adjacent convolutions 28.

Referring again to FIGS. 1 and 5, apparatus 10 includes wire feeding means 34 employing payout mechanism 36 for feeding and embedding electrically conductive wire 38 along leading edge 24 of each convolution or lap 28 just prior to application of bead 32 to tube 18 as shown. Wire 38 is shown in FIG. 2 partially imbedded in each ribbon convolution 28 and positioned adjacent leading edge 24, awaiting the laying on and heat-bonding of bead 32. For ease of explanation, both lap joints 29 and the V-shape of bead 32 are exaggerated in schematic FIG. 2. In reality, lap joints 29 are virtually coplanar heat bonds, and bead 32 forms an integral part of laps 38 at joints 29, completely encircling wire 38, as more clearly shown in FIGS. 3 and 8. The canting of winding rolls 14 causes tubing 18 to move continuously off winding means 12, defining the downstream direction of tubing 18 movement, as designated by directional arrow 39 in FIGS. 1 and 5. Cooling means including a conduit 13 (FIG. 6) within winding means 12 sprays water directed radially outwardly against the inner surface of the tubing 18, and also in a downstream direction which assists in discharging tubing 18 from winding means 12.

Figure 3:
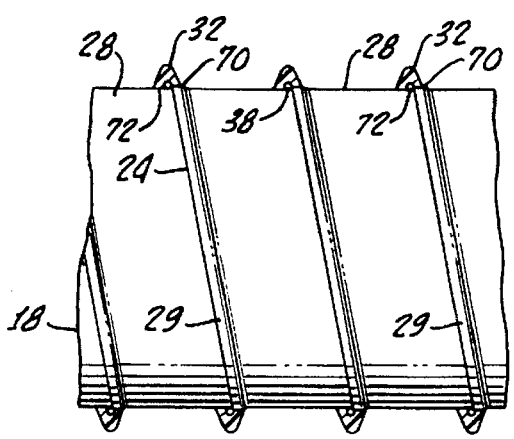
FIG. 3 is a fragmentary elevation view, partly in cross-section, of the tubing of the invention in an unflexed condition.
Figure 4:
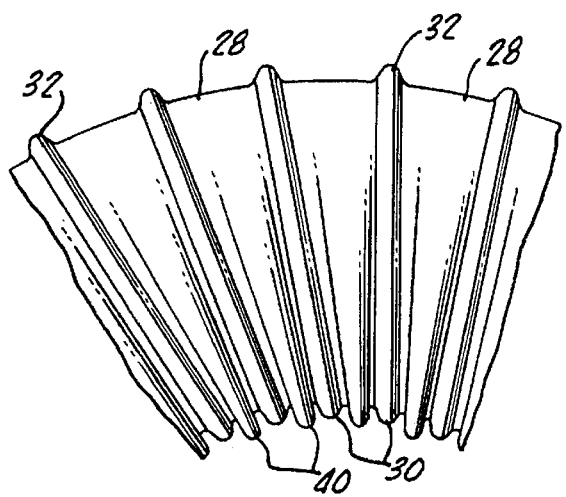
FIG. 4 is an elevation view of the tubing of FIG. 3 in a flexed condition.

The resulting tubing 18 is shown in more detail in FIGS. 3 and 4. FIG. 3 illustrates tubing 18 in an unflexed condition with bead 32 and wire 38 in cross-section, showing the relationship of bead 32 encapsulating wire 38 and covering lap joint 29. Bead 32 forms a smooth, crevice-free juncture with ribbon 38 on both sides of bead 32. FIG. 4 shows how tubing 18 may be bent to a small radius, forming buckles 40 on the inner side of the bend.

One specific arrangement for the wire feeding means is illustrated in FIG. 5. Trough 42 in extension arm 44 forms a guide for wire 38 as it is fed from a known payout mechanism 36 through wheel bearings or pulleys 46 mounted on base plate 48. Base plate 48 is secured to sliding block 50 which traverses mounting arm 52 and is restricted from lateral movement by face plate 58. Mounting arm 52 is clamped to a back plate 54 of winding means 12. Longitudinal placement of extension arm 44 relative to the axis 16 of winding means 12 is achieved by the sliding of block 50 along mounting arm 52 until wire 38 is positioned before extruded bead 32 at a leading edge 24 of a lap 28. Guiding rod 56 is fixed to sliding block 50 and extends through aperture 60 in vertical stop 62 mounted at the downstream end of mounting arm 52. Sliding block 50 is biased towards the upstream or winding means back plate end of mounting arm 52 by a coil spring 64 encircling guiding rod 56. Adjustment nut 66 at the downstream end 68 of guiding rod 56 is adjusted to fix extension arm 44 in place.

An extrudate such as HYTREL™ 5556 polyester elastomer is particularly suited for medical uses because of its purity, sterilizability, transparency and high strength. Because of the relatively low viscosity of such an extrudate, a vertical or near vertical draw angle from die to lap at powered rolls 14 is preferable. FIG. 6 illustrates draw angles from the vertical "α" and "β" for ribbon 22 and bead 32 respectively. Angles α and β preferably may be in the range of 0° to 45° depending on viscosity of extrudate and convenience of die placement, with 45° representing an experimentally preferable angle for both the bead 32 and the ribbon 22. As angles α and β approach 0°, the extrusion means for ribbon 22 and bead 32 are positioned successively closer to one another, and ultimately a single extruder may be used to provide both ribbon 22 and bead 32. On the other hand, with presently available materials having a greater melt viscosity and cohesiveness than HYTREL™, or with other materials which may become available in the future having such greater melt viscosity and cohesiveness, the angles α and β may be greater than 45° from the vertical. In other words, the draw angles α and β may approach or even pass the horizontal with a material having a sufficient body in its extrudate condition. Moreover, although ribbon 22 is illustrated in FIG. 6 as descending onto rolls 14 from the right of bead 32, it will be appreciated that ribbon 22 and bead 32 may descend as well from positions interchangeable with one another. Bead 32 is fed onto each lap 28 at a point following the draw point of wire 38 so that bead 32 heat bonds with lap 28 as it encapsulates wire 38.

Figure 7:
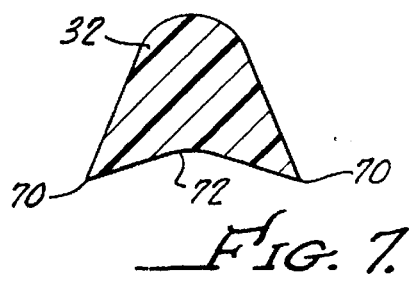
FIG. 7 is a section view of a bead portion of the flexible tubing product taken along line 7—7 of FIG. 5.

The cross-section of bead 32 is configured as shown in FIG. 7 to facilitate the smooth heat bonding of bead contact edges 70 with ribbon lap 28, while providing a recess 72 between edges 70 to accommodate wire 38 as wire 38 and bead 32 are sequentially drawn onto tubing 18. Splayed edges 70 provide a smooth interface with ribbon lap 28, as illustrated in FIG. 3, inhibiting the accumulation of microbes and particulate matter that are typical of the sharp angles resulting from traditional bead-forming practice.

Figure 8:
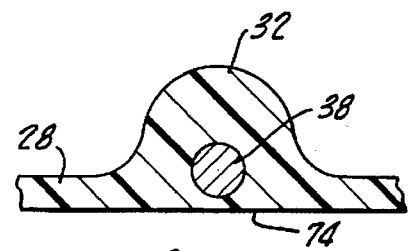
FIG. 8 is an enlarged section view of a wall portion of the tubing of FIG. 3 illustrating the unitary construction of the wall, bead and wire of the invention.

Heated bead 32 surrounds embedded wire 38 forming a unitary structure with ribbon lap 28 as shown in more detail in FIG. 8. The greater bulk of bead 32 is shown separating resistance wire 38 from the ambient environment, inhibiting loss of heat energy external to tubing 18 from resistance wire 38. Conversely, the separation between resistance wire 38 and the internal surface 74 of tubing 18 is minimal, facilitating efficient transfer of heat to the tidal fluid within the tubing 18 bore. In other words, the support bead 32 has a thickness and insulating value which is substantially greater than the ribbon 22. It follows that the support bead 32 both supports the wall of tube 18 against collapse and insulates the conductor 38 from ambient while heat from the conductor 38 is conducted inwardly of the tubing 18 through only a single thickness of the ribbon 22 forming the wall of the tube 18 adjacent to a lap joint 28.

Figure 9:
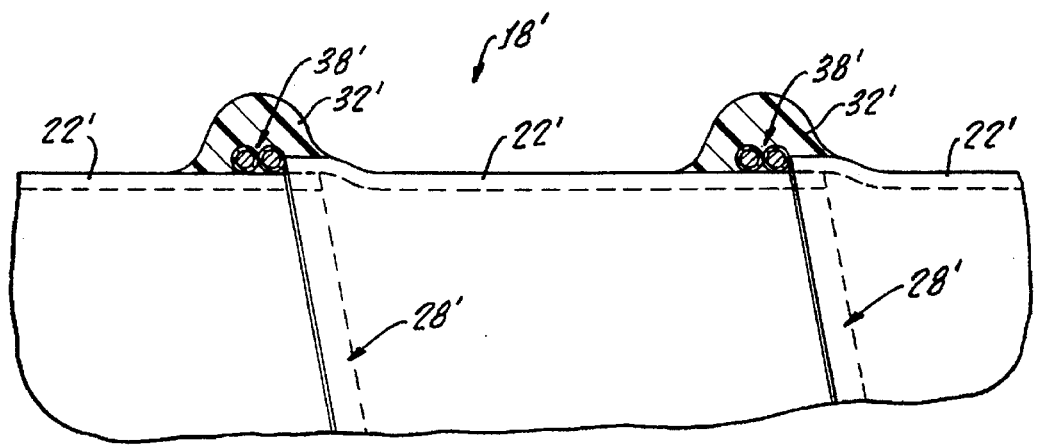
FIG. 9 provides an enlarged fragmentary cross-sectional view similar to FIG. 3, but showing an alternative embodiment of the invention.
Figure 10:
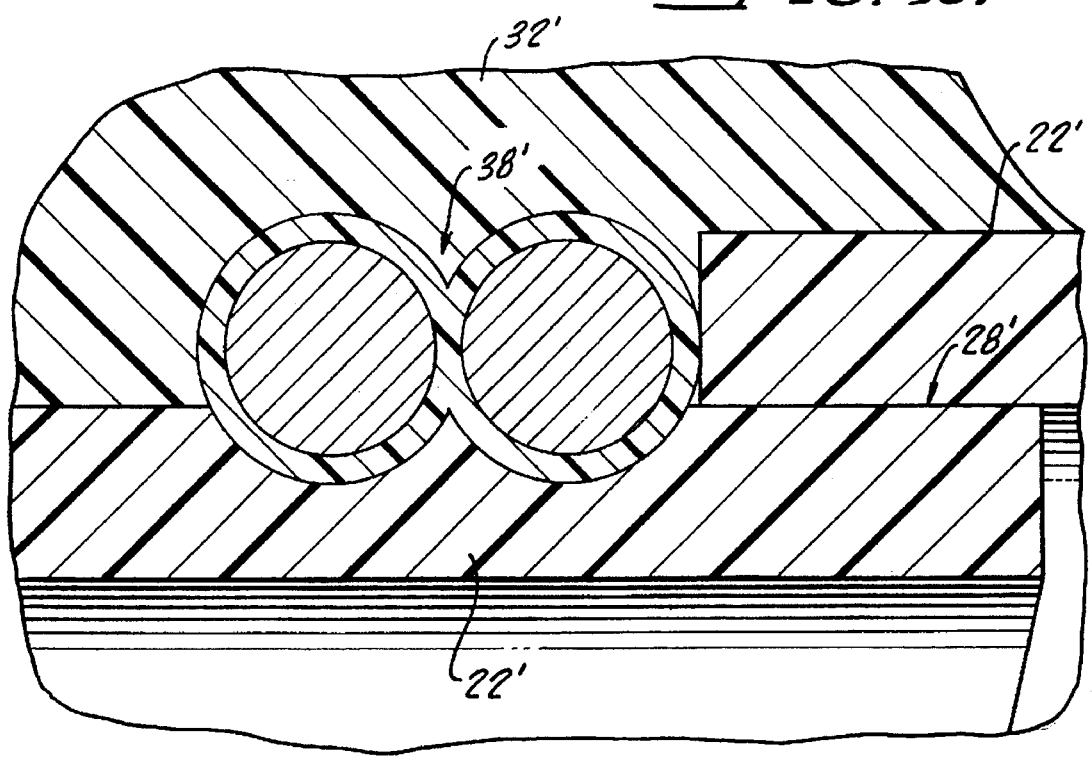
FIG. 10 is a greatly enlarged fragmentary view of a portion of FIG. 9.

Viewing now FIGS. 9 and 10, an alternative embodiment of the present invention is presented. In order to obtain reference numerals for use in describing the embodiment of FIGS. 9 and 10, features which are the same, or which are analogous in structure or function to those described above, are referenced with the same numeral used above, and having a prime added thereto.

FIGS. 9 and 10 in conjunction show that this embodiment of the tubing 18' includes flat film 22' helically wrapped on itself and overlapped to form a lap joint at 28' to form a thin walled flexible tube upon which a helical bead 32' is applied and integrally heat-bonded atop the joint 28'. Under the bead 32' and adjacent to an outer edge of the film 22' is positioned a heating conductor, generally referenced with the numeral 38'. However as FIGS. 9 and 10 depict, the conductor 38' is not a single conductor like conductor 38 of FIGS. 1–8. More particularly, heating conductor 38' includes a pair of parallel, but slightly spaced apart single heating conductors 74, which are carried in an insulating jacket 76. The conductors 74 may be similar to or the same as conductor 38 described above. Jacket 76 may be made of polyurethane, for example, and spans the spacing between the single conductors 74 so that the heating conductor 38' is in fact a small twin-lead cable construction.

During manufacture of the tubing construction 18' seen in FIGS. 9 and 10, the conductor 38' is fed into the depicted position just before the bead 32' is applied using a wire feeder like the device 34 depicted and described with respect to the first embodiment of the invention. However, the wire trough 42 is made wide enough to accept and guide the twin-lead conductor 38'.

An advantage of the tubing construction 18' seen in FIGS. 9 and 10 is that the two conductors 74 may be used to form opposite sides of a heating circuit. That is, electrical connections to the conductors 74 are made individually at one end of a length of the tubing 18'. Adjacent to the opposite end of the length of the tubing 18', the bead 32' is partially stripped away to expose the conductor 38'. Electrical connection between the conductors 74 is then effected at this location. As described, the tubing 18' has a particular advantage for use with a medical patient ventilator apparatus. That is, the electrical connections to the tubing can be effected at the proximal end near the ventilator. At the distal end of the length of tubing near the patient, connection of the conductors 74 to one another is all that is needed to complete the electrical heating circuit of the tubing 18.

While two exemplary forms of the invention have been shown in the drawings and described, variations from the exemplary forms will be apparent to those skilled in the art. The invention therefore should not be construed as limited to the specific forms shown and described, but instead as is set forth in the following claims.

What is claimed is:

1. A method for making a helically wound, flexible and collapse resistant seamless plastic tubing comprising the steps of:

forming an elongate ribbon of molten thermoplastic having opposite side edges, helically wrapping said elongate ribbon so that said opposite side edges overlap a certain distance to form a helical lap joint at which one of said opposite side edges is outwardly disposed, and simultaneously heat-bonding said ribbon to itself to form an elongate tubular body, using a single thickness of said elongate ribbon to define a wall for said tubing extending substantially between said helical lap joints;

laying an elongate, electrical heating conductor helically around and along said tubular body adjacent to said outwardly disposed one of said opposite side edges and atop said wall which is only a single thickness of said ribbon;

forming an elongate support bead of thermoplastic material having a thickness and insulating value which is substantially greater than said ribbon;

helically wrapping said support bead around and along said tubular body atop both said helical lap joint and said electrical conductor and simultaneously heat-bonding said support bead with said ribbon to form a unitary body including said ribbon and said bead with said electrical conductor embedded therebetween; and using said support bead to both support said tubular body against collapse and to insulate said electrical heating conductor from ambient while conducting heat from said electrical heating conductor inwardly of said tubing adjacent to said helical lap joint through said wall thereof which is only a single thickness of said ribbon.

2. The method of claim 1 wherein the step of forming and wrapping said elongate ribbon further comprises feeding said ribbon at a first draw angle tangential to said elongate tubular body, said first draw angle being in the range of 0° to 90° from the vertical.

3. The method of claim 2 wherein said first draw angle for said ribbon is 45°.

4. The method of claim 1 wherein the step of wrapping said elongate bead further comprises feeding said bead at a second draw angle tangential to said elongate tubular body, said second draw angle being in the range of 0° to 90° from the vertical.

5. The method of claim 4 wherein said second draw angle for said bead is 45°.

6. The method of claim 1 further including the step of selecting a nickel chromium alloy from which to form said electrical heating conductor.

7. The method of claim 6 still further including the step of forming said electrical heating conductor as a pair of parallel conductors spaced apart and insulated from one another.

8. The method of claim 7 also including the steps of forming said electrical heating conductor to include a jacket carrying said pair of conductors in spaced apart parallel relationship to one another to form a twin-lead heating cable, disposing said twin-lead heating cable with one of said pair of conductors adjacent to said outwardly disposed side edges of said elongate thermoplastic ribbon and with the other of said pair of conductors adjacent to said one conductor in side-by-side relationship with each conductor of said twin-lead cable separated from said thermoplastic ribbon only by said jacket, and conducting heat from said pair of conductors inwardly of said tubing only through said jacket and said wall of said tubing which is only a single thickness of said ribbon.

9. The method of claim 7 further including the step of electrically connecting together said pair of conductors adjacent to a distal end of a length of said tubing.

\* \* \* \* \*